United States Patent
Orbay (12)
(10) Patent No.: US 6,508,819 B1
(45) Date of Patent: Jan. 21, 2003

(54) METHOD OF DORSAL WRIST FRACTURE FIXATION

(75) Inventor: Jorge L. Orbay, Miami, FL (US)

(73) Assignee: Hand Innovations, Inc., Miami, FL (US)

( * ) Notice: Subject to any disclaimer, the term of this patent is extended or adjusted under 35 U.S.C. 154(b) by 0 days.

(21) Appl. No.: 09/941,119

(22) Filed: Aug. 28, 2001

(51) Int. Cl.$^7$ ............................................. A61B 17/80
(52) U.S. Cl. ........................................... 606/69; 606/60
(58) Field of Search ............................ 606/60, 69–73; 623/21.12

(56) References Cited

U.S. PATENT DOCUMENTS

| | | | | |
|---|---|---|---|---|
| 4,565,193 A | 1/1986 | Streli | ........................... | 128/92 |
| 4,651,724 A | 3/1987 | Berentey et al. | ............... | 128/92 |
| 4,867,144 A | 9/1989 | Kara et al. | ...................... | 128/92 |
| 5,190,544 A | 3/1993 | Chapman et al. | ............. | 606/69 |
| 5,197,966 A | 3/1993 | Sommerkamp | ............... | 606/69 |
| 5,586,985 A | 12/1996 | Putnam et al. | ................. | 606/69 |
| 5,853,413 A | 12/1998 | Carter et al. | ................... | 606/69 |
| 5,951,557 A | 9/1999 | Luter | ........................... | 606/69 |
| 5,964,763 A | 10/1999 | Incavo | ......................... | 606/71 |
| 6,096,040 A | 8/2000 | Esser | ........................... | 606/69 |
| 6,123,709 A | 9/2000 | Jones | ........................... | 606/69 |
| 6,129,730 A | 10/2000 | Bono et al. | ..................... | 606/73 |
| 6,221,073 B1 * | 4/2001 | Weiss et al. | ................... | 606/60 |
| 6,283,969 B1 * | 9/2001 | Grusin et al. | .................. | 606/69 |
| 2002/0032446 A1 * | 3/2002 | Orbay | ........................... | 606/69 |

FOREIGN PATENT DOCUMENTS

WO    WO97/47251    * 12/1997    ........... A61B/17/80

* cited by examiner

*Primary Examiner*—Nicholas D. Lucchesi
*Assistant Examiner*—Michael B. Priddy
(74) *Attorney, Agent, or Firm*—David P. Gordon; David S. Jacobson; Thomas A. Gallagher (57) ABSTRACT

A dorsal fracture is treated from the volar side by using a T-shaped plate opposite the fracture. The plate is positioned against the volar side of the radial bone, a plurality of bone screws secure the plate along a non-fractured portion of the radial bone, and a plurality of bone pegs extend from the plate and into the bone fragments of the fracture. A support portion of the plate is provided distal of the bone pegs and supports comminuted bone fragments. One or more channels are optionally provided in the plate to receive wires which are adapted to anchor distal bone fragments to the plate. The plate is adapted in strength and materials to withstand the large bending forces thereon.

14 Claims, 6 Drawing Sheets

METHOD OF DORSAL WRIST FRACTURE FIXATION

This application is related to U.S. Ser. No. 09/735,228, filed Dec. 12, 2000, which is a continuation-in-part of both U.S. Ser. No. 09/524,058, filed Mar. 13, 2000 and U.S. Ser. No. 09/495,854, filed Feb. 1, 2000, each of which are hereby incorporated by reference herein in their entireties.

BACKGROUND OF THE INVENTION

1. Field of the Invention

This invention relates broadly to surgical systems and methods. More particularly, this invention relates to a system and method for fracture fixation for a dorsal distal radius fracture.

2. State of the Art

Fractures of the wrist are difficult to align and treat. Alignment and fixation are typically performed by one of several methods: casting, external fixation, interosseous wiring, and plating. Casting is noninvasive, but may not be able to maintain alignment of the fracture where many bone fragments exist. Therefore, as an alternative, external fixators may be used. External fixators utilize a method known as ligamentotaxis, which provides distraction forces across the joint and permits the fracture to be aligned based upon the tension placed on the surrounding ligaments. However, while external fixators can maintain the position of the wrist, it may nevertheless be difficult in certain fractures to first provide the bones in proper alignment. In addition, external fixators are often not suitable for fractures resulting in multiple bone fragments. In addition, external fixation is associated with reflex sympathetic dystrophy, stiffness, and pin complications. Moreover, with some fractures, movement of the wrist is an essential part of rehabilitation, and this movement is prevented by external fixation. Interosseous wiring is an invasive procedure whereby screws are positioned into the various fragments and the screws are then wired together as bracing. This is a difficult and time consuming procedure. Moreover, unless the bracing is quite complex, the fracture may not be properly stabilized.

Volar wrist fractures (Colles' fractures) have been treated with a volar plate and screw system. The volar plate is generally a T-shaped plate having a head portion and a body portion. The body portion has holes along its length and the head portion has holes at its distal end. The holes are for receiving self-tapping bone screws therethrough. In use, the bone fragments of the volar wrist fracture are aligned and the body portion of the plate is screwed to an integral portion of the radius proximal of the fracture. Screws are then provided through the holes in the head portion to define a stabilizing framework about the fractured bone fragments heal.

Figure 1:
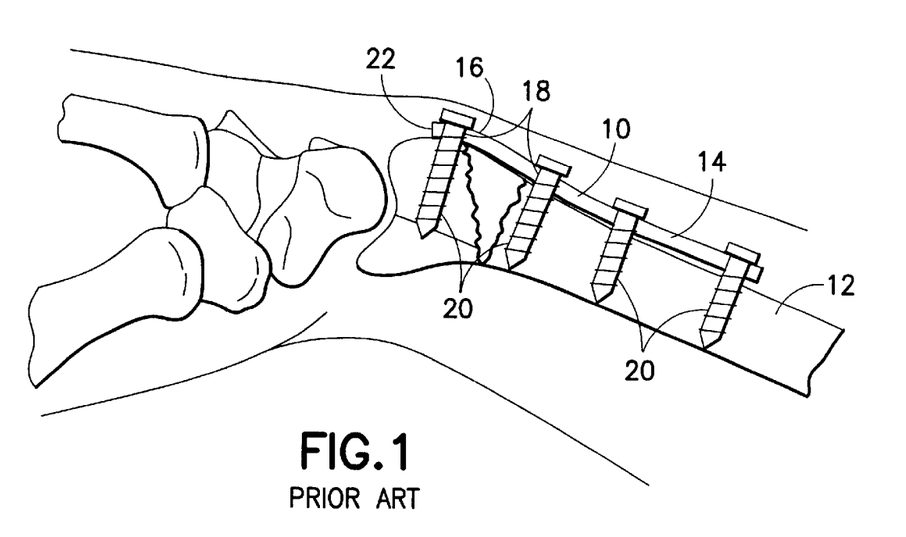
FIG. 1 is a dorsal wrist fracture and a prior art system for dorsal fracture fixation.

Dorsal wrist fractures have also been treated with a plate, but the plate is attached to the dorsal side of the radius. Referring to prior art FIG. 1, dorsal fixation has previously used a relatively thin plate 10 secured to the dorsal side of the radius 12. Like the volar plate, the dorsal plate 10 has a body portion 14 and a head portion 16. Holes 18 are provided in the both the body and head portions, and screws 20 extend therethrough into the radius 12 to compress the plate 10 against the bone and stabilize the fracture. The plate design, in terms of strength and support, has not been critical, as the forces on the dorsal plate from the tendons and bending forces are not substantially large. In fact, there is substantially no bending load on a dorsal plate. However, use of the dorsal plate commonly results in extensor tendon problems, as the extensor tendons run close to the bone surface and are irritated by the plate. In addition, it is common in distal radius fractures for one or more fragments, e.g., the radial styloid fragment, the volar dipunch fragment, and/or the dorsal dipunch fragment, to become loosened or detached from the bone system. It is necessary to stabilize these fragment to prevent further movement relative to the desired stabilizing arrangement and prevention of desired healing. Yet, stabilization of this bone with a dorsal plate is impractical, as the fragments are located on the opposite side of the bone from the dorsal plate. As such, a new dorsal wrist fracture fixation system is desired.

SUMMARY OF THE INVENTION

It is therefore an object of the invention to provide a fracture fixation system for a dorsal wrist fracture.

It is another object of the invention to provide dorsal fracture fixation in a manner which does not cause extensor tendon irritation.

It is also an object of the invention to provide a dorsal fracture fixation system which stabilizes distal radius bone fragments.

It is a further object of the invention to provide a dorsal fracture fixation system which provides stability and support to the fracture to overcome the forces from the tendons and rotational forces at the fracture.

In accord with these objects, which will be discussed in detail below, a dorsal fracture is treated from the volar side by using a fixation plate. The plate is generally a T-shaped plate defining an elongate body portion, a head portion transverse to the body portion, and a neck portion therebetween. The neck portion defines a fixed angle between the head and body portions. The plate also includes a first side intended to contact the bone, and a second side opposite the first side. The plate is substantially thick and rigid, and made of a high strength material such as titanium to resist the high bending loads to which a volar plate is subject in order to stabilize a dorsal fracture.

The head portion includes a plurality of threaded peg holes for receiving pegs therethrough. The center of the peg holes are preferably arranged along a line, with the axis of each peg hole preferably being in an oblique orientation relative to the axes of the other peg holes such that pegs therethrough are obliquely oriented relative to each other. According to one preferred aspect of the invention, at least half of the head portion extends on the distal side of the line defining a buttress on which to support bone fragments. The body portion includes a plurality of screw holes for the extension of the bone screws therethrough.

According to another preferred aspect of the invention, one or more channels extend in the first side of the head portion of the plate, preferably substantially parallel to the body portion. One or more wires are partially provided within the channels, and extend distally from the head portion of the plate to provide additional support for one or more bone fragments. The wires includes a distal means for anchoring to one or more bone fragments, and are coupled to their proximal ends of the plate.

According to another embodiment of the volar plate, the buttress comprises a plurality of tines, which may be bent to access and support distal articular fragments of a fracture.

In use, the plate is positioned with its first side against the volar side of the radius and bone screws are inserted through the bone screw holes into the radius to secure the volar plate to the radius. The bone fragments of the dorsal fracture are then aligned. A drill drills holes through the peg holes and into the bone fragments. The pegs are then inserted through the peg holes and into the holes in the bone, and threadably locked in position, with the head portion buttress supporting the bone fragments. The optional wires and tines also assist in bone fragment support. The structure of the plate, as well as the ability of fragment to slide along the bone pegs permits the plate to withstand the forces on the plate and provide a stabilizing structure which facilitates healing.

Additional objects and advantages of the invention will become apparent to those skilled in the art upon reference to the detailed description taken in conjunction with the provided figures.

BRIEF DESCRIPTION OF THE DRAWINGS

Prior art

DETAILED DESCRIPTION OF THE PREFERRED EMBODIMENTS

Figure 2:
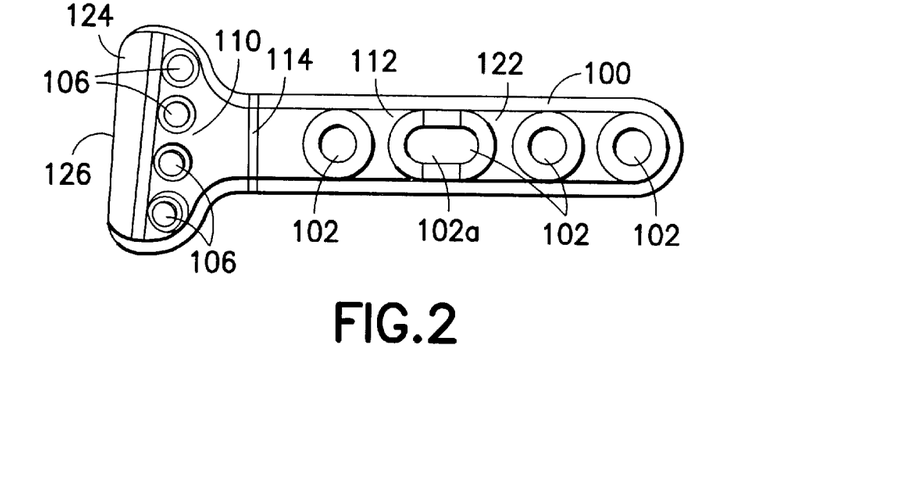
FIG. 2 is a top volar view of a right hand volar plate for dorsal wrist fracture according to a first embodiment of the invention.
Figure 3:
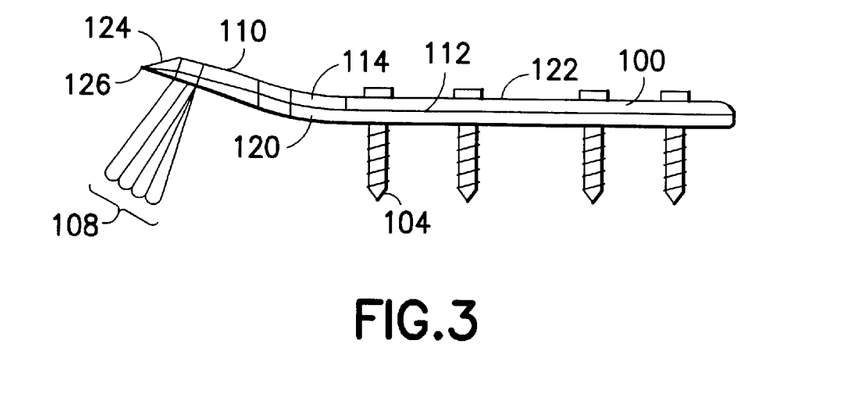
FIG. 3 is a side view of the plate of FIG. 2, shown with bone screws and pegs positioned therein.
Figure 4:
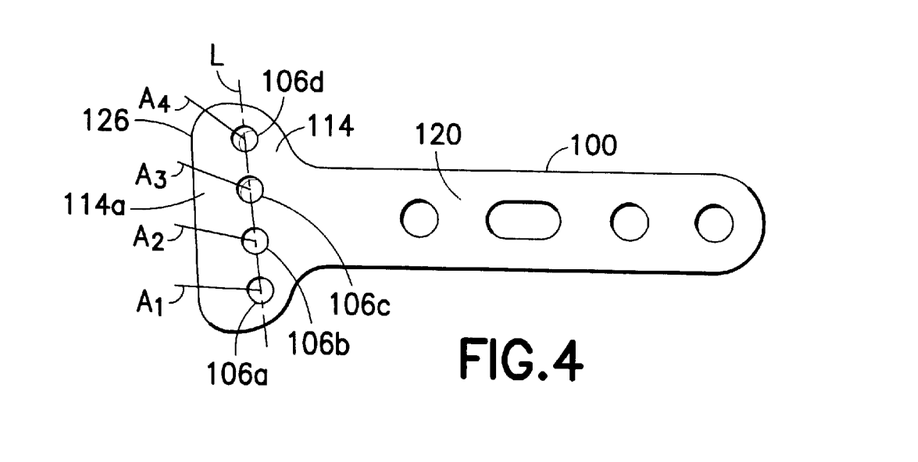
FIG. 4 is a bottom view of the plate of FIG. 2; the invention.

Turning now to FIGS. 2 through 4, a first embodiment of a volar plate system for dorsal wrist fracture fixation generally includes a substantially rigid T-shaped plate 100. The plate includes a plurality of holes 102 which receive self-tapping bone screws 104 to secure the plate 100 along a non-fractured portion of the radial bone. The plate also includes a plurality of threaded peg holes 106 which receive pegs 108 therein and are adapted to extend into bone fragments of the fracture.

The T-shaped plate 100 defines a head portion 110, an elongate body portion 112, and a neck portion 114 therebetween at which the head and body portions are angled relative to each other. A preferred angle is approximately 23° and the curvature of the neck portion is preferably at a radius of approximately one inch. The plate also includes a first side 120 which is intended to contact the bone, and a second side 122 opposite the first side. The first side 120 at the head portion is preferably planar, as is the first side at the body portion. As the head portion and body portion are angled relative to each other, the first side preferably defines two planar portions connected by the curved neck portion.

The plate 102 preferably has a thickness of approximately at least 2 mm at the head portion, and 2.5 mm along the body portion. A more preferred plate thickness is 4 to 6 mm, or more, at each of the body and head portions. The distal end 124 of the head portion is preferably tapered to provide a low distal profile and terminates at an edge 126. In addition, according to one preferred embodiment and not by way of limitation, the plate preferably has a width of 10 mm at the body portion, 11 mm at the neck portion, and 23 mm across line L of the head portion. The plate 102 is preferably made from a titanium alloy, such as Ti-6Al-4V.

The head portion 112 of the plate includes the threaded peg holes 106. In the preferred embodiment there are four threaded peg holes 106a, 106b, 106c, 106d (FIG. 4). The peg holes are preferably linearly arranged along the head portion 114, and are optionally provided such that the adjacent peg holes are provided further distally in a medial to lateral direction along the second side. As such, the centers of the peg holes lie along a line L (FIG. 4). According to another preferred aspect of the plate, each peg hole preferably defines an axis (axes $A_1$, $A_2$, $A_3$, and $A_4$ in FIG. 4) which is oblique (non-parallel) relative to the other peg holes such that pegs inserted therethrough are obliquely oriented relative to each other such that a fan-like shape is defined by the pegs (see FIG. 3). More particularly, and more preferably, the axes of the peg holes are angled in two dimensions (medial/lateral and proximal/distal) relative to each other; i.e., the pegs once inserted into the peg holes are also angled in two dimensions relative to each other. Preferred orientations of the axes of the peg holes are described in detail in previously incorporated U.S. Ser. Nos. 09/495,854 and 09/524,058. According to a preferred aspect of the invention, preferably at least half of the head portion (portion 114a) extends on the distal side of the line defined by the linear arrangement of peg holes (between the line L and the distal edge 126). This distal head portion 114a defines a buttress on which to support bone fragments, as described in more detail below.

The body portion 112 includes the plurality of screw holes 104 for the extension of the bone screws therethrough. Preferably one of the screw holes 102a (FIG. 2) is oblong.

Figure 5:
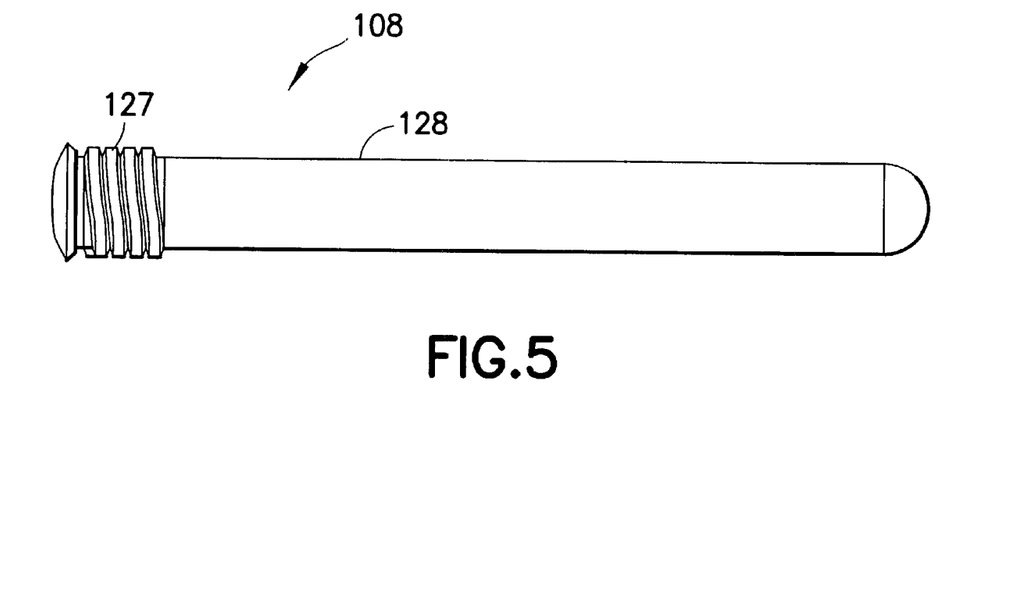
FIG. 5 is an enlarged side elevation of a first embodiment of a peg for use with the plate of the invention.
Figure 5A:
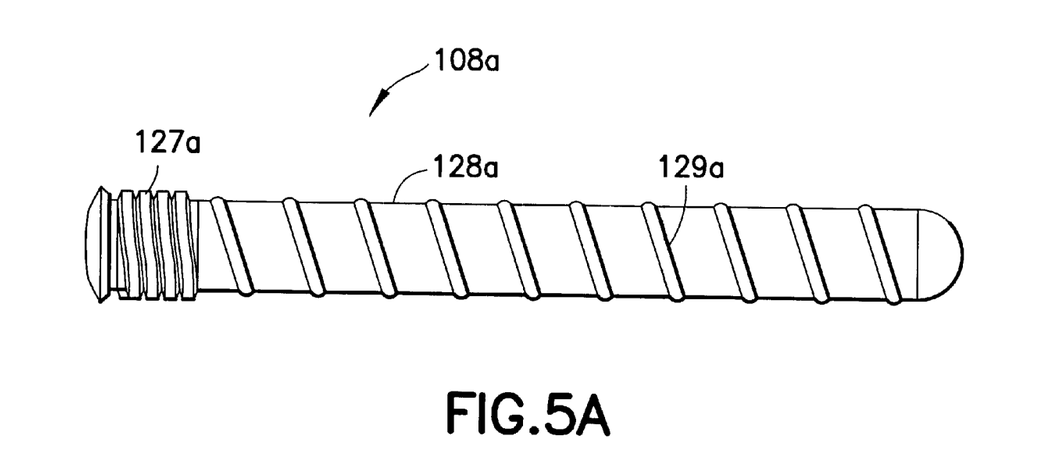
FIG. 5A is an enlarged side elevation of a second embodiment of a peg for use with the plate of the invention.

Referring to FIG. 5, each peg 108 has a non-tapered threaded head 127 and a substantially cylindrical shaft 128. The shaft 128 may be relatively smooth and non-threaded, as described in detail in previously incorporated, U.S. Ser. No. 09/524,058. Alternatively, referring to FIG. 5A, the peg 108a may include a shaft 128a provided with threads 129a. If the peg 108a includes a threaded shaft 128a, the threads 129a on the shaft are preferably of a different pitch than the threads on the head 127a. For example, the shaft 128a may include a pitch of twenty four threads per inch to aid in compression, while the head 127a may include a pitch of forty threads per inch for engagement in the peg holes. The pegs are preferably 2 mm in diameter.

Figure 6:
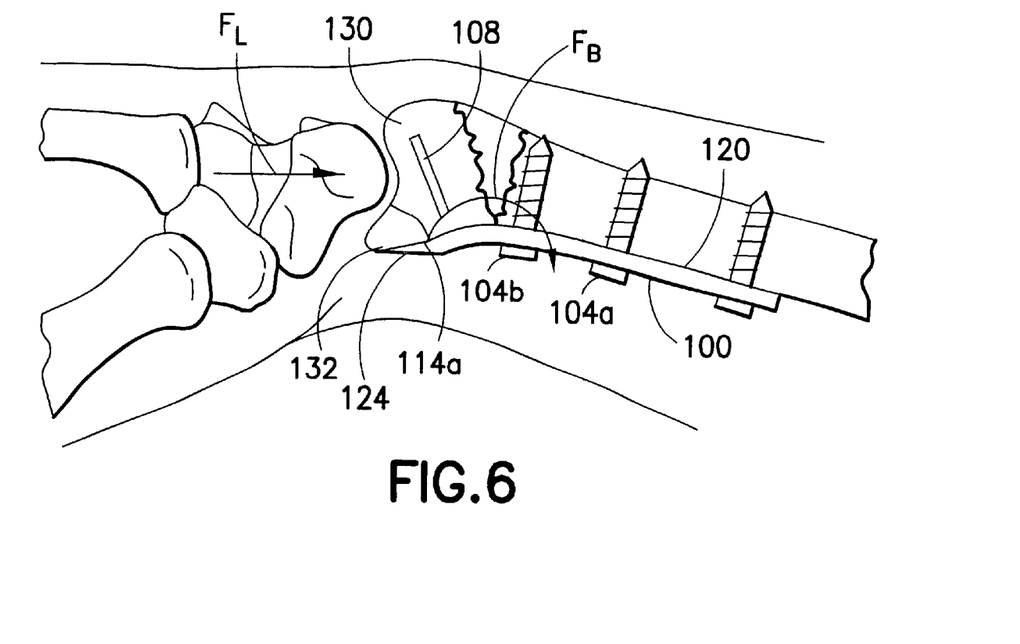
FIG. 6 is an illustration of the first embodiment of the plate according to the first embodiment of the invention provided in situ at the volar side of the radius for the treatment of a dorsal wrist fracture.

Referring now to FIG. 6, after a dorsal wrist fracture, the volar side of the wrist is opened (with tissue and muscle retracted from the volar side of the radius bone) and the plate 100 is positioned with its first side 120 against the volar side of the radius. A bone screw 104a is inserted through the oblong bone screw hole 102a (FIG. 2), but not completely tightened, to attach the plate to the radius. The plate 100 is moved relative to the screw 104a, and aligned relative to the radius and the fracture. The screw 104a in hole 102a is then tightened, and other screws are also provided in the other screw holes, as needed, to secure the plate to the radius. The taper at the distal end 124 substantially eliminates contact between the plate and the tendons thereabout, thereby preventing the tendon abrasion which commonly occurred with prior art dorsal plates.

The bone fragments 130, 132 (with 132 being the volar dipunch fragment) of the fracture are anatomically aligned as best as possible. Holes are then drilled through the peg holes, in alignment with the respective axes $A_1$, $A_2$, $A_3$, $A_4$ (FIG. 4), and into the fragments and interstices therebetween.

The pegs 108 are then inserted through the peg holes 106 (FIG. 2), and the heads of the pegs are threadably engaged in the plate. The pegs 108, extending through the oblique-axis peg holes are positioned immediately below the subcondylar bone of the radius. It is noted that the dorsal wrist fracture is a dorsally unstable fracture. The pegs 108, when not threaded, function as rails and permit the unstable distal bone fragments to move with one degree of freedom; that is, the fragments may only slide toward the volar side. Furthermore, in accord with the invention, the buttress 114a limits the sliding movement and provides support it for comminuted fragments, such as the volar dipunch 132, distal of the pegs.

Placing the plate 100 at the volar side for a dorsal fracture subjects the plate to substantially higher forces than a dorsal plate. The force $F_T$ of the tendons at the wrist places compressive forces on the plate, and movement of the wrist during postoperative healing and rehabilitation places high bending loads $F_B$ on the plate, particularly at the screw 104b closest the head portion. These forces are accommodated in at least two ways. First, as noted above, bone fragments are able to slide upon the pegs, rather than being fixed to the pegs. The advantage of this is discussed below with reference to FIG. 7. Second, as discussed below with respect to plates from other manufactures, the plate of the invention is designed to be stronger (substantially thicker and of stronger materials) than prior art plates. This increases the ability of the plate to withstand the bending forces to which it is subject.

Figure 7:
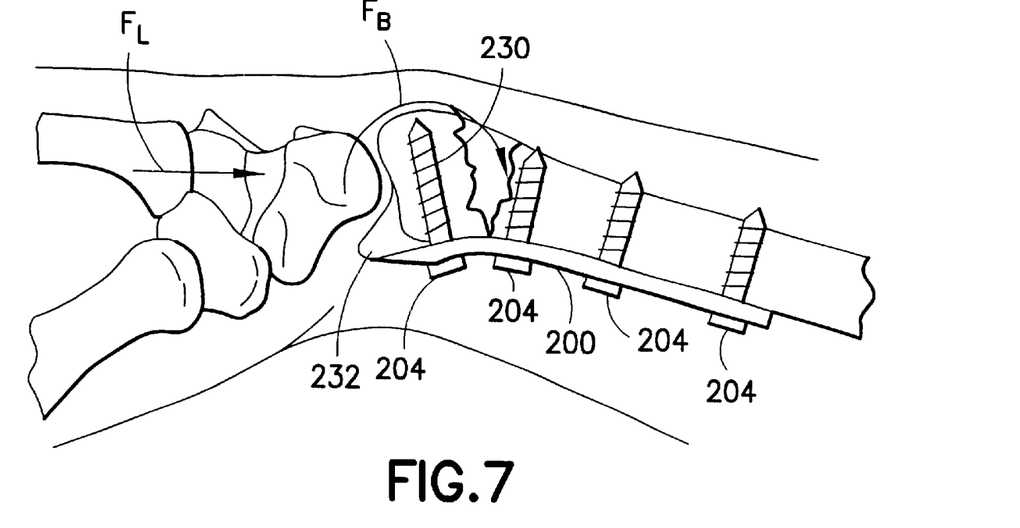
FIG. 7 is an illustration of the hypothetical use of a prior art volar plate used at the volar side of the radius for the treatment of a dorsal wrist fracture.

Referring to FIG. 7, for comparison purposes, it is shown that if a conventional volar or dorsal plate 200 is used according to the method described above, the same results would not be provided. Conventional plates use all screws 204 and no pegs. Bone fragments, e.g., 230, cannot slide upon the screws, as the screws tap into the bone fragments and fix the fragments in a location relative to the plate. This does to permit forces to be dissipated via sliding movement of the fragments and, as such, the plate is subject to much greater bending loads $F_b$ in addition to the compressive loads by the tendons $F_T$. Also, conventional plates do not have a buttress at the head portion in addition to pegs. As such, there is no support for any movable and unstable bone fragments distal of the screws, e.g., volar dipunch 232. Furthermore, the plate is substantially thinner and not constructed of materials adapted to withstand the forces on the volar side of the dorsal fracture. For example, the TT™ plate or volar-T™ plate available from Synthes of Paoli, PA, is made of a titanium alloy, but only 2 mm thick and 4 mm wide. The plate of the present invention is 3.5 times stronger than the Synthes plate, as measured by the ultimate load to failure. The SCS™ plate (subcondral support plate), available from Avanta of San Diegeo, Calif., is made of weaker stainless steel, and has a thickness of 1.5 mm and a width of 11 mm. Such plates are not suited for the forces the volar side treatment of a dorsal wrist fracture as plate failure would be relatively high.

Figure 8:
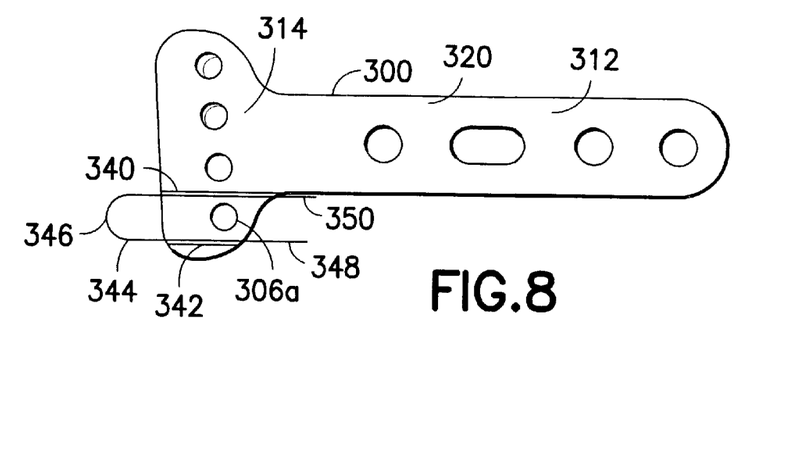
FIG. 8 is a bottom view of a volar plate and wire according to a second embodiment of the invention.

Turning now to FIG. 8, a second embodiment of a plate 300, substantially similar to the first embodiment (with like elements having reference numerals incremented by 200) is shown. The first side 320 of the head portion 314 of the plate 300 is provided with two channels 340, 342, one on either side of the medial-most peg hole 306a, which extend the length of the head portion. The channels 340, 342 are sized to receive a K-wire 344 therein. The K-wires is surgical grade wire preferably having a diameter of 0.062 inch. The K-wire 344 is preferably U-shaped, with the closed loop 346 provided distally and the free ends 348, 350 extending proximally through the channels and out thereof to extend along a length of the body portion 312 of the plate.

Figure 9:
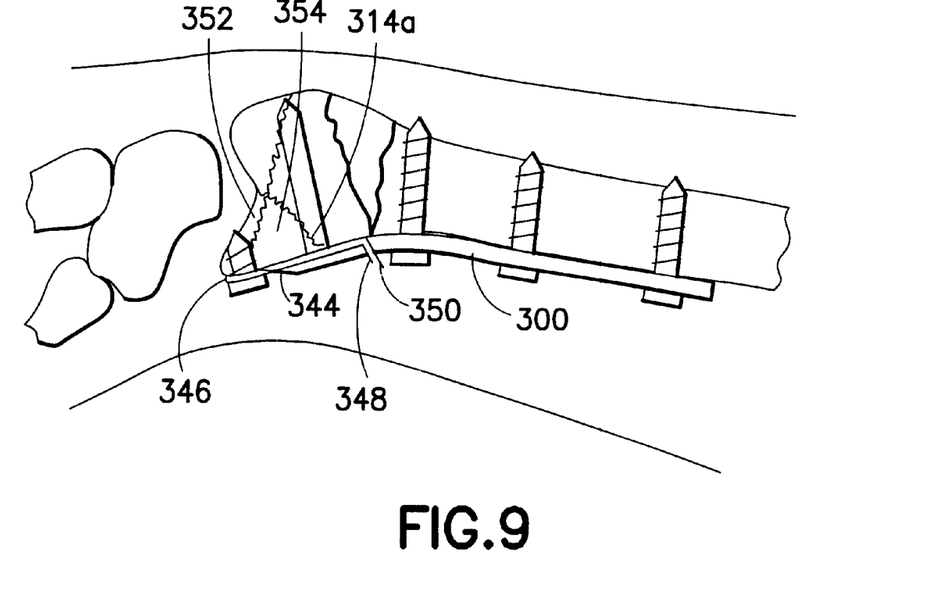
FIG. 9 is an illustration of the use of the volar plate and wire of FIG. 8 for the volar side treatment of a dorsal wrist fracture.

Referring to FIG. 9, the U-shaped K-wire 344 is provided in the channels as described above, and the plate is then attached to the radius as described above with respect to FIG. 6. The distal location loop can be adjusted by movement of the free ends to cause the loop to lie under one or more fragments, e.g., 352, 354 which is desired to be stabilized. A screw 356 having a head sized greater than the loop 346 is then positioned within the loop and tapped into the fragments to secure the fragments and K-wire together. The free ends 348, 350 of the wire are then tied off or otherwise secured to maintain the position of the loop relative to the plate. As such, a means is provided for stabilizing fragments located distal of the buttress by supporting and retaining the fragments.

Figure 10:
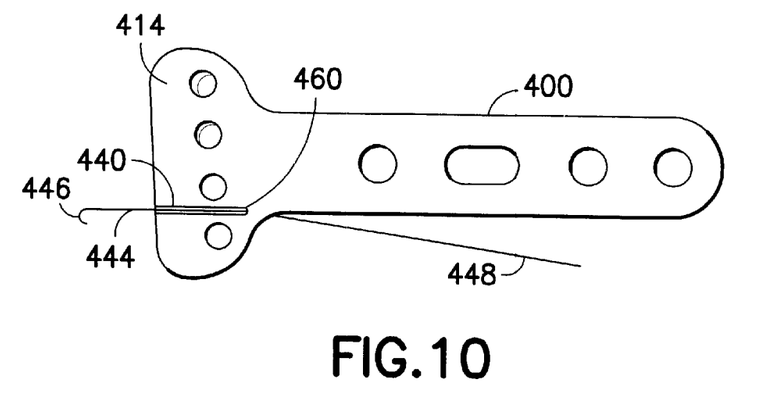
FIG. 10 is a bottom view of a volar plate and anchor according to a third embodiment of the invention.

Turning now to FIG. 10, a third embodiment of a plate 400, substantially similar to the second embodiment (with like elements having reference numerals incremented by 100 relative thereto) is shown. A channel 440 is provided in the head portion 414 of the plate 400 and extends only partly along the length of the head portion. A hole 460 is provided at the proximal end of the channel and extends to the second side of the plate. A single K-wire 444, provided with a distal anchor (or hook) 446 and a proximal end 448, extends within the channel and through the hole 460.

Figure 11:
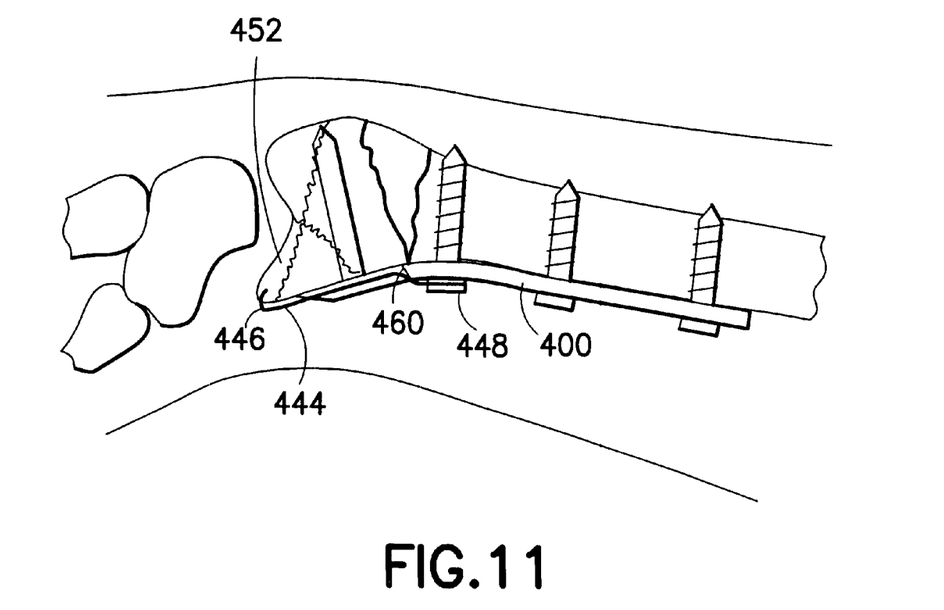
FIG. 11 is an illustration of the use of the volar plate and hook of FIG. 10 for the volar side treatment of a dorsal wrist fracture.

Referring to FIG. 11, the anchor 446 of the K-wire 444 is impacted into a fragment 452. If not previously threaded, the proximal end 448 of the wire 444 is then fed into the channel 440 and through the hole 460. The plate is then attached to the radius as described above with respect to FIG. 6. The wire 444 is then placed under tension (to constrain the distal fragment 452) and the proximal end 448 is secured, e.g., in a screw hole about the head of a screw.

Figure 12:
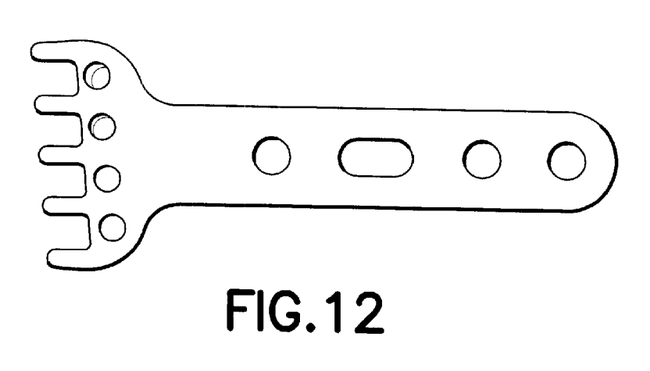
FIG. 12 is a bottom view of a volar plate according to a fourth embodiment of the invention.

Turning now to FIG. 12, a fourth embodiment of a plate 500, substantially similar to the first embodiment (with like elements having reference numerals incremented by 400) is shown. The head portion 510 distal of the peg holes 506 includes a plurality of tines 580. The tines 580 are preferably tapered in thickness relative to a remainder of the head portion, permitting each to be independently bent and substantially preventing tendon contact. As such, a configurable and individually customizable buttress structure useful in the support of distal fragments at a particular location is provided. Each tine is preferably approximately 7 mm in length and 2 mm in width, although other suitable dimensions (bendable by the physician, yet providing anatomical support) can be used. In use, the tines are bent by the physician into a configuration which will access and support the distal articular fragments. The plate is then attached to the radius as described above with respect to FIG. 6. Alternatively, though less desirably, the plate may first be attached to the radius and the tines then bent.

There have been described and illustrated herein embodiments of a system and method for stabilizing dorsal wrist fractures using a volar plate. While particular embodiments of the invention have been described, it is not intended that the invention be limited thereto, as it is intended that the invention be as broad in scope as the art will allow and that the specification be read likewise. Thus, while particular materials for the elements of the system have been disclosed, it will be appreciated that other materials may be used as well. In addition, while a particular number of screw holes in the volar plates and bone screws have been described, it will be understood another number of screw holes and screws may be provided. Further, fewer screws than the number of screw holes may be used to secure to the volar plate to the radius. Also, fewer or more peg holes and bone pegs may be used, preferably such that at least two pegs angled in two dimensions relative to each other are provided. Moreover, while the pegs are preferably linearly arranged, it will be appreciated that they may be non-linearly arranged, and may lie along a curve such as a parabolic curve, as described in previously incorporated U.S. Ser. Nos. 09/495,854 and 09/524,058. As such, the buttress portion is defined as the area distal the peg holes, whether or not the peg holes lie along a straight line. In addition, the pegs may be adjustable relative to the peg holes such that each peg can be independently fixed in a selectable orientation, as described in previously incorporated U.S. Ser. No. 09/735,228. Also, while a particular preferred angle between the head portion and body portion has been disclosed, other angles can also be used. While a right-handed plate is described with respect to the first embodiment, it will be appreciated that the volar plate for dorsal fixation may be formed in either a right- or left-handed model, with the left-handed model being a mirror image of the right-handed model described. Also, while two plate channel and K-wire assemblies have been disclosed for securing distal bone fragments to the plate, it will be appreciated that more than two channels and multiple K-wires may also be used, and that the channels may extend the length of the head portion or extend only part way, with an exit provided for the K-wire or K-wires. Furthermore, while two K-wire anchoring means having been disclosed (hooks and screws), it will be appreciated that other means for anchoring the K-wire into a bone fragment, e.g., nails, staples, additional K-wires, can be used as well. Also, other types of wires other than K-wires may be utilized. In addition, while preferred dimensions for a plate have been provided, it will be appreciated that other dimensions providing the substantially strong structure required to withstand the forces to which the plate when the plate is used in the manner of the method of the invention may also be used. It will therefore be appreciated by those skilled in the art that yet other modifications could be made to the provided invention without deviating from its spirit and scope as claimed.

What is claimed is:

1. A method of stabilizing a dorsal wrist fracture, comprising:

a) retracting tissue from a volar side of a radius bone; and b) attaching a stabilizing plate to the volar side of the radius bone substantially opposite the dorsal wrist fracture.

2. A method according to claim 1, wherein:

the plate includes screw holes and said attaching step includes providing screws through the screw holes and into the radius bone.

3. A method according to claim 1, further comprising:

c) inserting a plurality of pegs through threaded peg holes in a distal head portion of the plate and into a comminuted portion of the dorsal wrist fracture, the pegs being threadably secured in the peg holes.

4. A method according to claim 3, further comprising:

d) coupling a wire to both a distal fragment of the dorsal wrist fracture and the stabilizing plate.

5. A method according to claim 4, further comprising:

e) tensioning the wire.

6. A method according to claim 1, further comprising:

c) coupling a wire to a distal fragment of the dorsal wrist fracture and to the stabilizing plate.

7. A method according to claim 1, wherein:

the stabilizing plate includes a plurality of distal tines, said method further comprising,
bending the tines in a manner to support a distal fragment of the dorsal wrist fracture.

8. A method of stabilizing a dorsal wrist fracture, comprising:

a) providing a plate having an elongate body portion and a head portion transverse to the body portion, the body portion including a plurality of screw holes and the head portion including a plurality of threaded peg holes;

b) screwing a screw through one of the screw holes to attach the plate to a volar side of a radius bone substantially opposite the dorsal wrist fracture; and c) providing pegs through the plurality of peg holes and into at least one fragment of the fracture.

9. A method according to claim 8, further comprising:

d) prior to providing the pegs, drilling holes into the at least one fragment for the pegs.

10. A method according to claim 8, wherein:

the peg holes have axes which are oblique relative to each other, and the pegs extend along respective axes of the peg holes.

11. A method according to claim 8, wherein:

the peg holes have centers which are aligned.

12. A method according to claim 8, further comprising:

d) supporting one or more bone fragments with a buttress portion provided distal of the peg holes.

13. A method according to claim 12, further comprising:

e) stabilizing a distal bone fragment distal of the buttress portion.

14. A method according to claim 12, wherein:

said stabilizing includes coupling a wire to both the distal bone fragment and the plate.

* * * * *